(12) United States Patent
Brandman et al.

(10) Patent No.: US 10,815,479 B2
(45) Date of Patent: Oct. 27, 2020

(54) POOLED METHOD FOR HIGH THROUGHPUT SCREENING OF TRANS FACTORS AFFECTING RNA LEVELS

(71) Applicant: The Regents of the University of California, Oakland, CA (US)

(72) Inventors: Onn Brandman, San Francisco, CA (US); Jonathan Weissman, San Francisco, CA (US); Calvin H. Jan, San Francisco, CA (US); Luke A. Gilbert, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/175,977

(22) Filed: Jun. 7, 2016

(65) Prior Publication Data

US 2016/0362684 A1 Dec. 15, 2016

Related U.S. Application Data

(63) Continuation of application No. PCT/US2014/071119, filed on Dec. 18, 2014.

(60) Provisional application No. 61/917,480, filed on Dec. 18, 2013.

(51) Int. Cl.
| | |
|---|---|
| *C12N 15/86* | (2006.01) |
| *C12N 15/10* | (2006.01) |
| *C40B 20/04* | (2006.01) |

(52) U.S. Cl.
CPC ..... *C12N 15/1086* (2013.01); *C12N 15/1034* (2013.01); *C40B 20/04* (2013.01); *B01J 2219/00547* (2013.01); *B01J 2219/00572* (2013.01); *B01J 2219/00585* (2013.01); *B01J 2219/00722* (2013.01); *B01J 2219/00743* (2013.01)

(58) Field of Classification Search
None
See application file for complete search history.

(56) References Cited

U.S. PATENT DOCUMENTS

2008/0025958 A1 1/2008 Hannon et al.
2008/0312171 A1* 12/2008 Mallet .................. C12N 15/111
514/44 A

OTHER PUBLICATIONS

Mullokandov et al "High-throughput assessment of microRNA activity and function using microRNA sensor and decoy libraries" (Nature Methods Aug. 2012 vol. 9 No. 8: pp. 840-849).*
Mullokandov et al Supplementary Figures 1 to 6 Nature Methods vol. 9, No. 8, Aug. 2012 (Year: 2012).*
Brandman, O. et al. (Nov. 21, 2012). "A ribosome-bound quality control complex triggers degradation of nascent peptides and signals translation stress," *Cell* 151(5):1042-1054.
Gilbert, L.A. et al. (Jul. 18, 2013, e-published Jul. 11, 2013). "CRISPR-mediated modular RNA-guided regulation of transcription in eukaryotes," *Cell* 154(2):442-451.
International Search Report dated Mar. 13, 2015, for PCT Application No. PCT/US2014/071119, filed Dec. 18, 2014, 2 pages.
Kwasnieski, J.C. et al. (Nov. 20, 2012, e-published Nov. 5, 2012). "Complex effects of nucleotide variants in a mammalian cis-regulatory element," *Proc Natl Acad Sci USA* 109(47):19498-19503.
Larson, M.H. et al. (Nov. 2013, e-published Oct. 17, 2013). "CRISPR interference (CRISPRi) for sequence-specific control of gene expression," *Nat Protoc* 8(11):2180-2196.
Mali, P. et al. (Sep. 2013, e-published Aug. 1, 2013). "CAS9 transcriptional activators for target specificity screening and paired nickases for cooperative genome engineering," *Nat Biotechnol* 31(9):833-838.
Silva, J.M. et al. (Nov. 2005, e-published Oct. 2, 2005). "Second-generation shRNA libraries covering the mouse and human genomes," *Nat Genet* 37(11):1281-1288.
Written Opinion dated Mar. 13, 2015, for PCT Application No. PCT/US2014/071119, filed Dec. 18, 2014, 3 pages.

* cited by examiner

*Primary Examiner* — Catherine S Hibbert
(74) *Attorney, Agent, or Firm* — Mintz, Levin, Cohn, Ferris, Glovsky and Popeo, P.C.

(57) ABSTRACT

Provided herein are methods directed to multiplexed detection of the modulation of transcriptional activity using perturbation elements.

16 Claims, 3 Drawing Sheets

POOLED METHOD FOR HIGH THROUGHPUT SCREENING OF TRANS FACTORS AFFECTING RNA LEVELS

CROSS-REFERENCES TO RELATED APPLICATIONS

This application is a continuation of PCT Application No. PCT/US2014/071119, filed Dec. 18, 2014 which claims priority to U.S. Provisional Application No. 61/917,480, filed Dec. 18, 2013, which are incorporated by reference herein in their entirety.

BACKGROUND

Many cellular pathways are poorly understood and genetic screens (e.g. via RNAi) combined with pathway specific phenotypic readouts are a powerful and common way to investigate them. Currently most methods for pathway specific screens use multi well microplates, robots, and plate readers. This is expensive and cumbersome. Thus, there is need for alternative methods not involving these technologies. Provided herein are methods and compositions addressing these and other needs in the art.

SUMMARY

Provided herein, inter alia, is a method of multiplexed detection of modulation of transcriptional activity caused by a plurality of perturbation elements. The method includes introducing a plurality of delivery vectors into a cell culture. Each delivery vector within the plurality of delivery vectors individually includes a perturbation element identifying DNA sequence operatively linked to a promoter of interest and a perturbation element-encoding DNA sequence operatively linked to a constitutive promoter. The cells of the cell culture include approximately one delivery vector per cell. The cell culture is allowed to express the plurality of delivery vectors. The expression forms a plurality of perturbation element identifying RNA sequences from the perturbation element identifying DNA sequences and a plurality of perturbation elements from the perturbation element-encoding DNA sequences. Each perturbation element within the plurality of perturbation elements is allowed to modulate transcriptional activity of each corresponding promoter of interest. An amount of each perturbation element identifying RNA sequence within the plurality of perturbation element identifying RNA sequences is detected. The amount of each perturbation element identifying RNA sequence within the plurality of perturbation element identifying RNA sequences is compared to an amount of each corresponding perturbation element identifying DNA sequences, thereby detecting modulation of transcriptional activity caused by each of the plurality of perturbation elements.

Also provided is a method of multiplexed quantitative detection of modulation of transcriptional activity caused by a plurality of perturbation elements. The method includes introducing a plurality of delivery vectors into a cell culture. Each delivery vector within the plurality of delivery vectors individually includes a perturbation element identifying DNA sequence operatively linked to a promoter of interest and a RNA-perturbation element-encoding DNA sequence operatively linked to a constitutive promoter. The cells of the cell culture integrate approximately one delivery vector per cell. The cell culture is allowed to express the plurality of delivery vectors. The expression forms a plurality of perturbation element identifying RNA sequences from the perturbation element identifying DNA sequences and a plurality of RNA perturbation elements from the perturbation element-encoding DNA sequences. Each RNA perturbation element within the plurality of perturbation elements is allowed to modulate transcriptional activity of each corresponding promoter of interest. The cells in the cell culture are lysed and the nucleic acids are extracted from the lysate. Each perturbation element identifying RNA sequence within the plurality of perturbation element identifying RNA sequences is sequenced, thereby determining an amount of each perturbation element identifying RNA sequence. The amount of each perturbation element identifying RNA sequence is compared to an amount of each corresponding perturbation element identifying DNA sequences, thereby quantitatively detecting modulation of transcriptional activity caused by each of the plurality of perturbation elements.

Provided are DNA constructs that include a perturbation element identifying DNA sequence operatively linked to a promoter of interest and a perturbation element-encoding DNA sequence operatively linked to a constitutive promoter. The perturbation element identifying DNA sequence operatively linked to a promoter of interest and the perturbation element-encoding DNA sequence operatively linked to a constitutive promoter are operatively linked.

Provided is a kit for multiplexed quantitative detection of modulation of transcriptional activity caused by a plurality of perturbation elements. The kit includes a plurality of delivery vectors. Each delivery vector within the plurality of delivery vectors individually includes a perturbation element identifying DNA sequence operatively linked to a promoter of interest and a perturbation element-encoding DNA sequence operatively linked to a constitutive promoter. The kit also includes a first oligonucleotide primer substantially complementary to and hybridizable with the perturbation element identifying DNA sequence. The kit also includes a second oligonucleotide primer substantially complementary to and hybridizable with a perturbation element identifying RNA sequence expressed from the perturbation element identifying DNA sequence.

BRIEF DESCRIPTION OF THE DRAWINGS

FIG. 3A shows the result of qPCR after 20 minutes and 60 minutes of heat shock to monitor barcode expression. Results were compared to a genomically integrated HSF1 reporter. Barcode levels were normalized to total mRNA. FIG. 3B shows sgRNA effectively targets TEF1 promoter driving Venus fluorescent protein expression. Fluorescence was measured by flow cytometry for strains without sgRNA ("Vector"), with a sgRNA expressed alone on a plasmid (Ctl. sgRNA), and with the induced barcode reporter ("Reporter"). The dead Cas9-Mxi1 fusion enhances the transcription inhibition of dead Cas9 (normalized to sgRNA-free control).

DETAILED DESCRIPTION

Figure 1:
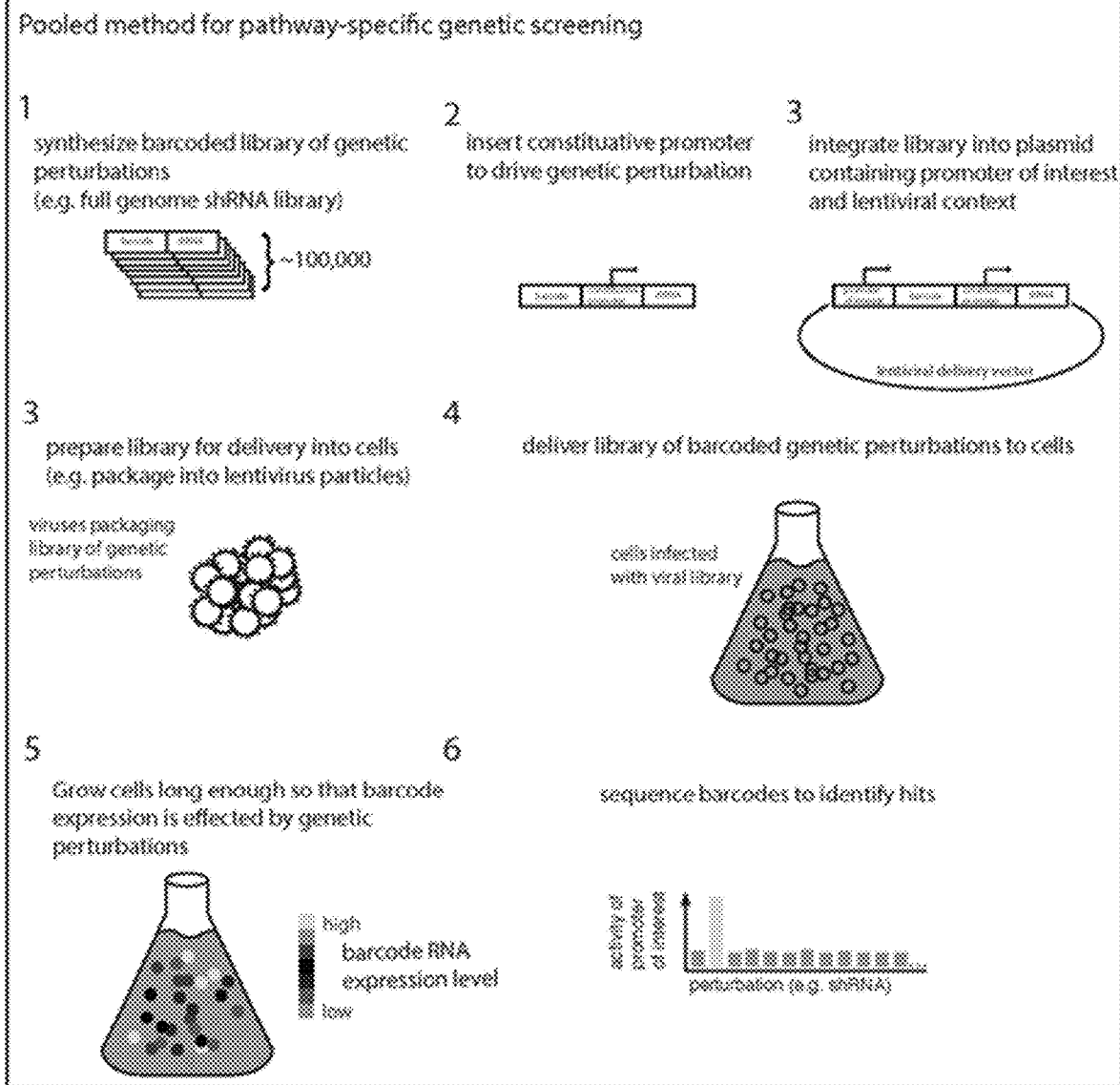
FIG. 1 is a schematic demonstrating an exemplary method provided herein employing shRNAs. Briefly, a series of barcodes are synthesized and combined with a perturbation element in a plasmid or cassette. The plasmids are delivered to cells in culture and given time to express the barcode and perturbation element. The cells are lysed and the nucleic acids sequenced to identify and quantify perturbation elements influencing activity.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

"Nucleic acid" refers to deoxyribonucleotides (DNA) or ribonucleotides (RNA) and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The word "polynucleotide" refers to a linear sequence of nucleotides. The nucleotides can be ribonucleotides, deoxyribonucleotides, or a mixture of both. Examples of polynucleotides contemplated herein include single and double stranded DNA, single and double stranded RNA (including miRNA), and hybrid molecules having mixtures of single and double stranded DNA and RNA. A "3'-UTR" refers to the 3'-untranslated region of an mRNA that immediately follows the translation stop codon.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The word "expression" or "expressed" as used herein in reference to a DNA nucleic acid sequence (e.g. a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual*, 18.1-18.88). Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion the gene is positioned between two transposon linker sequences that allow insertion into the host genome as well as subsequent excision. "Extracting nucleic acids" refers to processes well known in the art to purify or otherwise separate or isolate a nucleic acid (e.g. RNA or DNA) from a mixture (e.g. a cell lysate).

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids. A "viral plasmid" as used herein refers to a plasmid having a viral origin (e.g. a retrovirus). A "2-micron plasmid" refers to a yeast 2-micron circularized plasmid. A "CEN/ARS plasmid" refers to a plasmid constructed to propagate in two different host species and can include an autonomously replicating sequence and a yeast centromere.

A "delivery vector" as used herein, refers to a plasmid or other polynucleotide that includes the sequences of interest (e.g. a perturbation element-encoding DNA) that is introduced into a cell. Optionally, a delivery vector is a plasmid as described herein. Optionally, a delivery vector is a retroviral delivery vector (e.g. lentirviral). Thus, delivery vectors can be any nucleotide construction used to deliver nucleic acids into cells (e.g., a plasmid), or as part of a general strategy to deliver genes, e.g., as part of recombinant retrovirus or adenovirus (Ram et al. Cancer Res. 53:83-88, (1993)). As used herein, plasmid or viral vectors are agents that transport the disclosed nucleic acids into the cell without degradation and include a promoter yielding expression of the appropriate gene or perturbation element in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector.

The viral vectors can include nucleic acid sequence encoding a marker product. This marker product is used to determine if the gene has been delivered to the cell and once delivered is being expressed. Preferred marker genes are the *E. Coli* lacZ gene, which encodes B galactosidase, and fluorescent proteins, e.g., Venus fluorescent protein or green fluorescent protein. Optionally, the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure.

Construction of suitable vectors employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

A "cell," as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization. Optionally, the cell is one grown in cell and/or tissue culture.

"Control" or "control experiment" is used in accordance with its plain ordinary meaning and refers to an experiment in which the subjects or reagents of the experiment are treated as in a parallel experiment except for omission of a procedure, reagent, or variable of the experiment. Optionally, the control is used as a standard of comparison in evaluating experimental effects. Optionally, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "modulator" refers to a composition that increases or decreases the level of a target molecule or the function of a target molecule or the physical state of the target of the molecule.

The term "modulate," "modulation," or "modulator," as used with reference to modulating an activity of a target gene or signaling pathway, refers to increasing (e.g., activating, facilitating, enhancing, agonizing, sensitizing, potentiating, or upregulating) or decreasing (e.g., preventing, blocking, inactivating, delaying activation, desensitizing, antagonizing, attenuating, or downregulating) the activity of the target gene or signaling pathway. In some embodiments, a modulator increases the activity of the target gene or signaling pathway, e.g., by at least about 1-fold, 2-fold, 3-fold, 4-fold, 5-fold, 6-fold, 7-fold, 8-fold, 9-fold, 10-fold, 15-fold, 20-fold or more. In some embodiments, a modulator decreases the activity of the target gene or signaling pathway, e.g., by at least about 1-fold, 2-fold, 3-fold, 4-fold, 5-fold, 6-fold, 7-fold, 8-fold, 9-fold, 10-fold, 15-fold, 20-fold or more.

The terms "promoter," "promoter region," or "promoter sequence," refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping e.g., with nuclease S1), as well as protein binding domains (consensus sequences) responsible for the binding of RNA polymerase.

A promoter is "constitutive" when the gene being transcribed is expressed (e.g. continually expressed) independent of perturbations in the cellular process.

A "promoter of interest" is a promoter sensitive to perturbations in the cellular process (e.g. binding to components of the cell such as translation factors that form part of the cellular machinery performing the cellular function that is being perturbed by the perturbation factor).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

A "perturbation element" as used herein refers to a nucleic acid sequence, e.g., a RNA sequence, or a DNA sequence, or a polypeptide sequence, an amino acid sequence, or a protein that interferes with the function of a cell (e.g. through interruption of a signaling pathway, interruption of the localization of proteins or nucleotides, interference of post-translational modifications including phosphorylation, or through changes to degradation rates of target molecules). A "nucleic acid perturbation element" is a perturbation element containing a nucleic acid sequence, e.g., DNA, RNA or a combination thereof. A nucleic acid perturbation element can be an inhibitory nucleic acid, an aptamer, a ribozyme, a triplex forming molecule or an external guide sequence. An "RNA perturbation element" is a perturbation element containing RNA, for example, in a stem loop configuration that is capable of altering or disrupting cellular functions such as transcription factor activation. An RNA perturbation element may be an inhibitory nucleic acid, e.g., shRNA, miRNA, siRNA, or CRISPR guide RNA. Optionally, the RNA perturbation element is an antisense molecule or a ribozyme. A "protein perturbation element" is a perturbation element containing a polypeptide sequence, e.g., an antibody. The protein can be full-length or a variant thereof (e.g. having at least 70%, 80%, 90%, 95%, 96%, 97%, 98%, 99% identity). A protein perturbation element may alter or disrupt cellular functions through protein interactions with other cellular components.

An "inhibitory nucleic acid" is a nucleic acid (e.g. DNA, RNA, polymer of nucleotide analogs) that is capable of binding to a target nucleic acid and reducing transcription of the target nucleic acid (e.g. mRNA from DNA) or reducing the translation of the target nucleic acid (e.g. mRNA) or altering transcript splicing (e.g. single stranded morpholino oligo). A "morpholino oligo" may be alternatively referred to as a "morphlino nucleic acid" and refers to morpholine-containing nucleic acid nucleic acids commonly known in the art (e.g. phosphoramidate morpholinio oligo or a "PMO"). See Marcos, P., Biochemical and Biophysical Research Communications 358 (2007) 521-527. In some embodiments, the "inhibitory nucleic acid" is a nucleic acid that is capable of binding (e.g. hybridizing) to a target nucleic acid and reducing translation of the target nucleic acid. Optionally, the target nucleic acid reduces the transcription of the target nucleic acid. The target nucleic acid is or includes one or more target nucleic acid sequences to which the inhibitory nucleic acid binds (e.g. hybridizes). Thus, an inhibitory nucleic acid typically is or includes a sequence that is capable of hybridizing to at least a portion of a target nucleic acid at a target nucleic acid sequence. An example of an inhibitory nucleic acid is an antisense nucleic acid. Another example of an inhibitory nucleic acid is siRNA or RNAi (including their derivatives or pre-cursors, such as nucleotide analogs). Further examples include shRNA, miRNA, shmiRNA, or certain of their derivatives or pre-cursors. In some embodiments, the inhibitory nucleic acid is single stranded. In other embodiments, the inhibitory nucleic acid is double stranded.

An "siRNA" refers to a nucleic acid that forms a double stranded RNA, which double stranded RNA has the ability to reduce or inhibit expression of a gene or target gene when the siRNA is present (e.g. expressed) in the same cell as the gene or target gene. The siRNA is typically about 5 to about 100 nucleotides in length, more typically about 10 to about 50 nucleotides in length, more typically about 15 to about 30 nucleotides in length, most typically about 20-30 base nucleotides, or about 20-25 or about 24-29 nucleotides in length, e.g., 20, 21, 22, 23, 24, 25, 26, 27, 28, 29, or 30 nucleotides in length. siRNA molecules and methods of generating them are described in, e.g., Bass, 2001, Nature, 411, 428-429; Elbashir et al., 2001, Nature, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, Molecular Interventions, 2:158 (2002).

The siRNA can be administered directly or siRNA expression vectors can be used to induce RNAi that have different design criteria. A vector can have inserted two inverted repeats separated by a short spacer sequence and ending with a string of T's which serve to terminate transcription.

The term "miRNA" refers to a microRNA molecule found in eukaryotes that is involved in gene regulation. See, e.g., Carrington et al., Science 301(5631):336-8 (2003), which is hereby incorporated by reference. Names of miRNAs and their sequences are provided herein.

Clustered regularly interspaced short palindromic repeats (CRISPRs) are DNA loci containing short repetitions of base sequences. They are associated with cas genes that code for proteins related to CRISPRs. This system can be used in a manner analogous to RNAi to control gene expression. Typically, the Cas9 protein is used in conjunction with a CRISPR guide RNA that targets a gene of interest and interferes with transcription. More specifically, co-expression of dCas9 and a sgRNA blocks transcription by interfering with transcriptional elongation, RNA polymerase binding, or transcription factor binding. The system is known and has been described in Larson, et al., *Nature Protocols* 8:2180-2196 (2013), and U.S. Publication No. 2014/0068797, which are incorporated by reference herein in their entirety. Thus, the CRISPRi system can be customized for any desired gene of interest.

A "perturbation element-encoding DNA sequence" as used herein is a DNA encoding the RNA sequence or amino acid sequence for a perturbation element.

A "perturbation element identifying DNA sequence" or "DNA barcode" as used herein refers to a sequence of nucleotides uniquely associated with individual perturbation elements and encodes a "perturbation element identifying RNA sequence" enabling identification of active perturbation elements. In some embodiments, the perturbation element identifying RNA sequence is detected using sequencing techniques (e.g. deep sequencing).

A "perturbation element identifying RNA sequence" or "RNA barcode" as used herein refers to a sequence of nucleotides uniquely associated with individual perturbation elements and enables identification of active perturbation elements. Optionally, the perturbation element identifying RNA sequence is detected using sequencing techniques (e.g. deep sequencing).

A "protein binding RNA sequence" as used herein refers to a sequence of RNA, typically a stem loop or portion thereof, able to bind (e.g. specifically bind) to a RNA binding protein. A protein binding RNA sequence can be a viral protein binding RNA sequence such as MS2 coat protein binding RNA sequence, or PP7 coat protein binding RNA sequence.

A "protein binding-perturbation identifying RNA" as used herein refers to an RNA sequence including a protein binding RNA sequence and perturbation element identifying RNA sequence. The protein binding-perturbation identifying RNA may also include a RNA perturbation element or an RNA sequence encoding a protein perturbation element.

An "RNA binding protein" as used herein refers to a protein capable of binding (e.g. specifically binding) to an RNA sequence (e.g. a protein binding RNA sequence). The RNA sequence can be single or double stranded. Examples of RNA binding proteins include but are not limited to MS2 protein or PP7 protein. An RNA binding protein typically includes at least one "RNA binding domain" capable of selective recognition of a RNA sequence (e.g. a protein binding RNA sequence).

A "viral RNA binding protein" as used herein refers to a RNA binding protein having a viral origin. Viral RNA binding proteins include MS2 coat protein or PP7 coat protein.

As used herein, a "protein-perturbation identifying RNA complex" refers to an RNA binding protein bound to a protein binding-perturbation identifying RNA. Detection of the active perturbation element can be performed by identifying the RNA complexed with the RNA binding protein in a purified or isolated protein-perturbation identifying RNA complex (e.g. sequencing of the RNA barcode).

An "auxiliary-DNA sequence" refers to a DNA sequence encoding a stable polynucleotide. An auxiliary-DNA sequence may be translated to a polypeptide. Optionally, the presence of an auxiliary-DNA sequence promotes stability of the RNA transcript containing the barcode or perturbation element.

The term "an amount of" in reference to a polynucleotide or polypeptide, refers to an amount of a component or element is detected. The amount may be measured against a control, for example, wherein an increased level of a RNA barcode following exposure to a perturbation element in relation to its corresponding perturbation element identifying DNA sequence demonstrates enrichment of the barcode. In contrast, a decreased level of a RNA barcode following exposure to a perturbation element in relation to its corresponding perturbation element identifying DNA sequence demonstrates non-enrichment of the barcode. The amount of a component may be decreased through such pathways as proteasomal degradation or increased through such pathways as enhanced promoter activity. The measure of enrichment or non-enrichment may be performed with pooled cells. The amount may be a frequency count of the number of RNA barcodes.

Provided herein, inter alia, is a method of multiplexed detection of modulation of transcriptional activity caused by a plurality of perturbation elements. The method includes introducing a plurality of delivery vectors into a cell culture. Each delivery vector within the plurality of delivery vectors individually includes a perturbation element identifying DNA sequence operatively linked to a promoter of interest and a perturbation element-encoding DNA sequence operatively linked to a constitutive promoter. The cells of the cell culture integrate one delivery vector per cell. The cell culture is allowed to express the plurality of delivery vectors. The expression forms a plurality of perturbation element identifying RNA sequences from the perturbation element identifying DNA sequences and a plurality of perturbation elements from the perturbation element-encoding DNA sequences. Each perturbation element within the plurality of perturbation elements is allowed to modulate transcriptional activity of each corresponding promoter of interest. An amount of each perturbation element identifying RNA sequence within the plurality of perturbation element identifying RNA sequences is detected. The amount of each perturbation element identifying RNA sequence within the plurality of perturbation element identifying RNA sequences is compared to an amount of each corresponding perturbation element identifying DNA sequences, thereby detecting modulation of transcriptional activity caused by each of the plurality of perturbation elements.

The term "multiplexed" as used herein refers to multiple identifiable perturbation element identifying DNA sequences pooled into a cell culture that can be individually assessed using the unique perturbation element identifying DNA sequence. Thus, the method permits simultaneous detection of modulation of transcriptional activity caused by a plurality of perturbation elements. A cell used in the methods herein, includes a cell carrying out metabolic or other function sufficient to preserve or replicate its genomic DNA. A cell culture is a plurality of cells grown under a desired condition. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization. Optionally, the cell is one grown in cell and/or tissue culture. Optionally, the cell is one isolated from a plant or animal (e.g. human). Optionally, the cell may be a terminally differentiated cell.

Each of the cells, optionally, includes a single different perturbation element identifying DNA sequence and a single different perturbation element-encoding DNA sequence. Optionally the cells are lysed before the detection step.

The delivery vector may be a plasmid, such as a viral plasmid, 2-micron plasmid, or CEN/ARS plasmid, as described herein. Optionally, the delivery vector is a viral plasmid. The viral plasmid may be a lentiviral plasmid. The delivery vector may be a retroviral delivery vector. The delivery vector may be a lentiviral delivery vector. The delivery vector may further include an auxiliary-DNA sequence operatively linked to the perturbation element identifying DNA sequence. Optionally, the auxiliary-DNA sequence is operatively linked to a 5' end of the perturbation element identifying DNA sequence. The perturbation element identifying DNA sequence may be located in the 3'-UTR of the auxiliary-DNA sequence. Optionally, the auxiliary-DNA sequence is operatively linked to a 5' end of the perturbation element-encoding DNA sequence. The perturbation element-encoding DNA sequence may be located in the 3'-UTR of the auxiliary-DNA sequence.

The delivery vector may include a terminator sequence 3' of the perturbation element identifying DNA sequence. Optionally, the delivery vector may include a terminator sequence 3' of the perturbation element-encoding DNA sequence. Optionally, the delivery vector does not include a terminator sequence 3' of the perturbation element identifying DNA sequence. Optionally, the delivery vector does not include a terminator sequence 3' of the perturbation element-encoding DNA sequence.

The promoter of interest may be a promoter regulated by a transcription factor. The promoter of interest may be a promoter involved in a signaling pathway. The promoter of interest may be operatively linked to either the 5' end or 3' end of the perturbation element identifying DNA sequence. Optionally, the promoter of interest is operatively linked to the 5' end of the perturbation element identifying DNA sequence. Optionally, the promoter of interest is operatively linked to the 3' end of the perturbation element identifying DNA sequence.

The constitutive promoter may be operatively linked to either the 5' end or 3' end of the perturbation element-encoding DNA sequence. Optionally, the constitutive promoter is operatively linked to the 5' end of the perturbation element-encoding DNA sequence. In embodiment, the constitutive promoter is operatively linked to the 3' end of the perturbation element-encoding DNA sequence.

The promoter of interest, the perturbation element identifying DNA sequence, the perturbation element-encoding DNA sequence and the constitutive promoter can be within a cassette (e.g. a single continuous DNA sequence) or within multiple cassettes. The promoter of interest may be operatively linked to a 5' end of the perturbation element identifying DNA sequence, the constitutive promoter may be linked to a 3' end of the perturbation element identifying DNA sequence, and the perturbation element-encoding DNA sequence may be operatively linked to a 3' end of the constitutive promoter. Optionally, constitutive promoter may be operatively linked to the 5' end of the perturbation element-encoding DNA sequence, the perturbation element-encoding DNA sequence may be operatively linked to the 5' end of the promoter of interest, and the promoter of interest may be operatively linked to the 5' end of the perturbation element identifying DNA sequence. Optionally, the constitutive promoter is located 5' of inducible promoter. Optionally, the constitutive promoter and promoter of interest are pointing away from each other or pointing towards each other. Optionally, the perturbation element is a CRISPR guide RNA. Optionally, the cassette further includes a DNA sequence encoding the Cas9 gene.

The perturbation element identifying DNA sequence may be about 15 nucleotides to about 500 nucleotides in length. The perturbation element identifying DNA sequence may be about 15 nucleotides to about 250 nucleotides in length. The perturbation element identifying DNA sequence may be about 15 nucleotides to about 200 nucleotides in length. The perturbation element identifying DNA sequence may be about 15 nucleotides to about 100 nucleotides in length. The perturbation element identifying DNA sequence may be about 15 nucleotides to about 75 nucleotides in length. The perturbation element identifying DNA sequence may be about 15 nucleotides to about 50 nucleotides in length. The perturbation element identifying DNA sequence may be about 15 nucleotides to about 40 nucleotides in length. The perturbation element identifying DNA sequence may be about 15 nucleotides to about 30 nucleotides in length. The perturbation element identifying DNA sequence may be about 15 nucleotides to about 25 nucleotides in length. Thus, the perturbation element identifying DNA sequence may be about 15, 16, 17, 18, 19, 20, 21, 22, 23, 24, 25, 26, 27, 28, 29, or 30 nucleotides in length.

Optionally, the perturbation element identifying DNA sequence may be at least 5, 10, 15, 16, 17, 18, 19, 20, 21, 22, 23, 24, 25, or 30 nucleotides in length.

The perturbation element identifying DNA sequence may be expressed as a perturbation element identifying RNA sequence. Optionally, the expression is controlled by the promoter of interest. Thus, when the promoter of interest is perturbed by the perturbation element, the transcriptional activity of the perturbation element identifying DNA sequence into a perturbation element identifying RNA sequence is reduced. Optionally, when the promoter of interest is perturbed by the perturbation element such that its level of transcription is increased (e.g. the perturbation element enhances the transcriptional activity of the promoter of interest), the transcriptional activity of the perturbation element identifying DNA sequence into a perturbation element identifying RNA sequence is increased. Optionally, comparing an amount of the perturbation element identifying RNA sequence to its corresponding perturbation element identifying DNA sequence detects the influence or modulation of the promoter of interest by the perturbation element (e.g. increased ratio of RNA to DNA indicates greater expression than in the absence of the perturbation element and increased transcriptional activity).

The perturbation element may be a RNA perturbation element or a protein perturbation element. The perturbation element may be a protein perturbation element. The perturbation element may be a RNA perturbation element. Thus, optionally, the perturbation element is shRNA, miRNA, siRNA, or CRISPR guide RNA. The perturbation element may be shRNA. The perturbation element may be miRNA. The perturbation element may be siRNA. The perturbation element may be CRISPR guide RNA. Methods for making and using CRISPR guide RNA are known and described in, for example, Larson, et al., Nature Protocols 8:2180-2196 (2013), and U.S. Publication No. 2014/0068797, which are incorporated by reference herein in their entirety.

Optionally, the perturbation element modulates a cellular function of the cell thereby modulating expression of a transcription factor. Optionally, the transcription factor regulates the promoter of interest.

Detecting an amount of each perturbation element identifying RNA sequence within the plurality of perturbation element identifying RNA sequences can include sequencing the plurality of perturbation element identifying RNA sequences and counting the frequency of each perturbation element identifying RNA sequence within the plurality of perturbation element identifying RNA sequences. An increased count of a perturbation element identifying RNA sequence relative to an amount of its corresponding perturbation element identifying DNA sequence may indicate increased transcriptional activity. A decreased count of a perturbation element identifying RNA sequence relative to an amount of its corresponding perturbation element identifying DNA sequence may indicated decreased transcriptional activity. Optionally, the sequencing is done using deep sequencing techniques known in the art.

Methods for detecting RNA are largely cumulative with the nucleic acid detection assays and include, for example, Northern blots, RT-PCR, arrays including microarrays and sequencing including high-throughput sequencing methods. In some embodiments, a reverse transcriptase reaction is carried out and the targeted sequence is then amplified using standard PCR. Quantitative PCR (qPCR) or real time PCR (RT-PCR) is useful for determining relative expression levels, when compared to a control. Quantitative PCR techniques and platforms are known in the art, and commercially available (see, e.g., the qPCR Symposium website, available at qpersymposium.com). Nucleic acid arrays are also useful for detecting nucleic acid expression. Customizable arrays are available from, e.g., Affymatrix.

Optionally, methods for detecting RNA include sequencing methods. RNA sequencing are known and can be performed with a variety of platforms including, but not limited to, platforms provided by Illumina, Inc., (La Jolla, Calif.) or Life Technologies (Carlsbad, Calif.). See, e.g., Wang, et al., Nat Rev Genet. 10(1):57-63 (2009); and Martin, Nat Rev Genet. 12(10):671-82 (2011). Optionally, methods for detecting RNA including miRNA include microarray methods, which are known and can be performed with a variety of platforms including, but not limited to, platforms provided by Ambion, Inc., (Austin, Tex.) and Life Technologies (Carlsbad, Calif.).

Also provided herein is a method of multiplexed quantitative detection of modulation of transcriptional activity caused by a plurality of perturbation elements. The method includes introducing a plurality of delivery vectors into a cell culture. Each delivery vector within the plurality of delivery vectors individually includes a perturbation element identifying DNA sequence operatively linked to a promoter of interest and a RNA-perturbation element-encoding DNA sequence operatively linked to a constitutive promoter. The cells of the cell culture integrate one delivery vector per cell. The cell culture is allowed to express the plurality of delivery vectors. The expression forms a plurality of perturbation element identifying RNA sequences from the perturbation element identifying DNA sequences and a plurality of RNA-perturbation elements from the perturbation element-encoding DNA sequences. Each RNA-perturbation element within the plurality of perturbation elements is allowed to modulate transcriptional activity of each corresponding promoter of interest. The cells in the cell culture are lysed and the nucleic acids are extracted from the lysate. Each perturbation element identifying RNA sequence within the plurality of perturbation element identifying RNA sequences is sequenced, thereby determining an amount of each perturbation element identifying RNA sequence. The amount of each perturbation element identifying RNA sequence is compared to an amount of each corresponding perturbation element identifying DNA sequences, thereby quantitatively detecting modulation of transcriptional activity caused by each of the plurality of perturbation elements.

The delivery vector is as described hereinabove, including embodiments thereof. The petrubation element identifying DNA sequence is as described hereinabove, including embodiments thereof. The cells and cell culture are as described hereinabove, including embodiments thereof. Cell may be lysed using conventional methods known in the art. Nucleic acids may be extracted from cell lysates using conventional methods known in the art. The perturbation elements are as described hereinabove, including embodiments thereof. The sequencing of the nucleic acids is as described hereinabove, including embodiments thereof. The perturbation element-encoding DNA sequence is as described hereinabove, including embodiments thereof.

Provided are DNA constructs that can be used in the provided methods. Thus, DNA constructs are provided that include a perturbation element identifying DNA sequence operatively linked to a promoter of interest and a perturbation element-encoding DNA sequence operatively linked to a constitutive promoter. The perturbation element identifying DNA sequence operatively linked to a promoter of interest and the perturbation element-encoding DNA sequence operatively linked to a constitutive promoter are operatively linked. The perturbation element may be a RNA perturbation element or a protein perturbation element. The perturbation element may be a protein perturbation element. The perturbation element may be a RNA perturbation element. Thus, optionally, the perturbation element is shRNA, miRNA, siRNA, or CRISPR guide RNA. The perturbation element may be shRNA. The perturbation element may be miRNA. The perturbation element may be siRNA. The perturbation element may be CRISPR guide RNA.

Also provided is a kit for multiplexed quantitative detection of modulation of transcriptional activity caused by a plurality of perturbation elements. The kit includes a plurality of delivery vectors. Each delivery vector within the plurality of delivery vectors individually includes a perturbation element identifying DNA sequence operatively linked to a promoter of interest and a perturbation element-encoding DNA sequence operatively linked to a constitutive promoter. The kit also includes a first oligonucleotide primer substantially complementary to and hybridizable with the perturbation element identifying DNA sequence. The kit also includes a second oligonucleotide primer substantially complementary to and hybridizable with a perturbation element identifying RNA sequence expressed from the perturbation element identifying DNA sequence. The peturbation element is as described hereinabove, including embodiments thereof. The delivery vector is as described hereinabove, including embodiments thereof. The perturbation element identifying DNA sequence is as described hereinabove, including embodiments thereof. The perturbation element-encoding DNA sequence is as described hereinabove, including embodiments thereof. Optionally, the kit may also include a third oligonucleotide primer substantially complementary to and hybridizable with the perturbation element-encoding DNA sequence. The kit may optionally include materials for PCR, such as but not limited to buffers, deoxynucleotide triphosphates, cations (e.g. monovalent or divalent), and a polymerase.

The kit can further include marker detection agents, such as marker specific primers or probes attached to an addressable array. Kits can also include components for comparing results such as a suitable control sample, for example a positive and/or negative control. The kit can also include a collection device for collecting and/or holding samples. Optionally, the provided kits include instructions for use.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims below.

EXAMPLES

Example 1

Pooled Method for High Throughput Quantification of the Effects of Perterbations on Transcriptional Activity Herein is described a pooled method for high throughput quantification of the effects of genetic perturbations on a pathway-specific transcriptional readout. This method allows for the identification of trans factors that effect RNA synthesis/metabolism/degradation. This can be achieved by creating a barcoded shRNA library where the barcode is expressed by a promoter of interest and the shRNA is constitutively expressed and delivering the barcoded shRNA library to cells. The barcode RNA is isolated and sequenced to identify genetic perturbations that effect transcriptional readout. This pooled, pathway specific method requires no cellular manipulation, and therefore enables high coverage and multiplexing of several readouts. Thus, compared to existing pathway-specific pooled methods, the provided methods offer superior performance including higher precision, increased library coverage, and the ability to multiplex different readouts in the same screen. This is because there is no cell enrichment (e.g. cell sorting) step required.

A library of DNA constructs is synthesized so that each construct contains a genetic perturbation (e.g. shRNA targeting a specific gene) and DNA barcode (e.g., an approximately 20 nucleotide sequence). To span the entire human genome using RNAi this library will consist of approximately 100,000 uniquely barcoded constructs (approximately 5 per gene), each targeting a different sequence in the transcriptome. Each construct can be a relatively short, e.g., approximately, 200 nucleotides in length. A constitutive promoter is inserted into the library to drive expression of the genetic perturbation using Gateway® cloning (Life Technologies, Carlsbad, Calif.). The constructs are ligated into a retroviral delivery vector that also contains a pathway-specific promoter poised to drive expression of the barcode. The retroviral delivery vector may be a lentiviral delivery vector. The library is packaged into retrovirus (e.g. lentivirus). A culture of cells is infected so that each cell integrates one construct into its genome.

Once inside cells, the barcodes will begin to be transcribed proportionally to the activity of the pathway of interest. Perturbations will also take effect and potentially modulate the signaling pathway of interest and therefore barcode levels. The diversity of perturbations causes transcription of the barcodes to vary between cells with different perturbations; barcodes will be enriched by perturbations that increase pathway activity, dis-enriched by perturbations that decrease pathway activity. Cells are lysed, and RNA and DNA are extracted. Deep sequencing is used to count the frequencies of RNA barcodes (concentration is proportional to pathway activity) and DNA barcodes (one per infected cell). The ratio of RNA/DNA for each barcode reveals its enrichment under a specific perturbation and thus pathway activity in that condition. A schematic of an exemplary method is shown in FIG. 1.

The above strategy allows for a genome-wide, pathway-specific screen to be performed and processed in two weeks. The scheme described has several key features and extensions. First, the strategy can be applied to any cell type that can be infected by a retrovirus (e.g. lentivirus). Since lentiviral libraries can be frozen, screening a new cell type or growth condition does not require regeneration of the library. This means that primary cell lines, cell lines from patients with pathologies, and cancer lines can all be screened with relative ease. Since pathway activity and not cellular division are assayed, cells do not need to divide to be screened, and thus terminally differentiated cells may be screened and studied. Furthermore, multiple transcriptional readouts can be screened in the same culture flask and therefore subject to identical conditions, which increases the quality of the integrated data set. As long as readouts drive differing barcodes they can be multiplexed, allowing potentially hundreds of readouts to be screened in parallel at the same time.

Example 2

Multiplexed Analysis Using Pooled High Complexity CRISPRi

Figure 2:
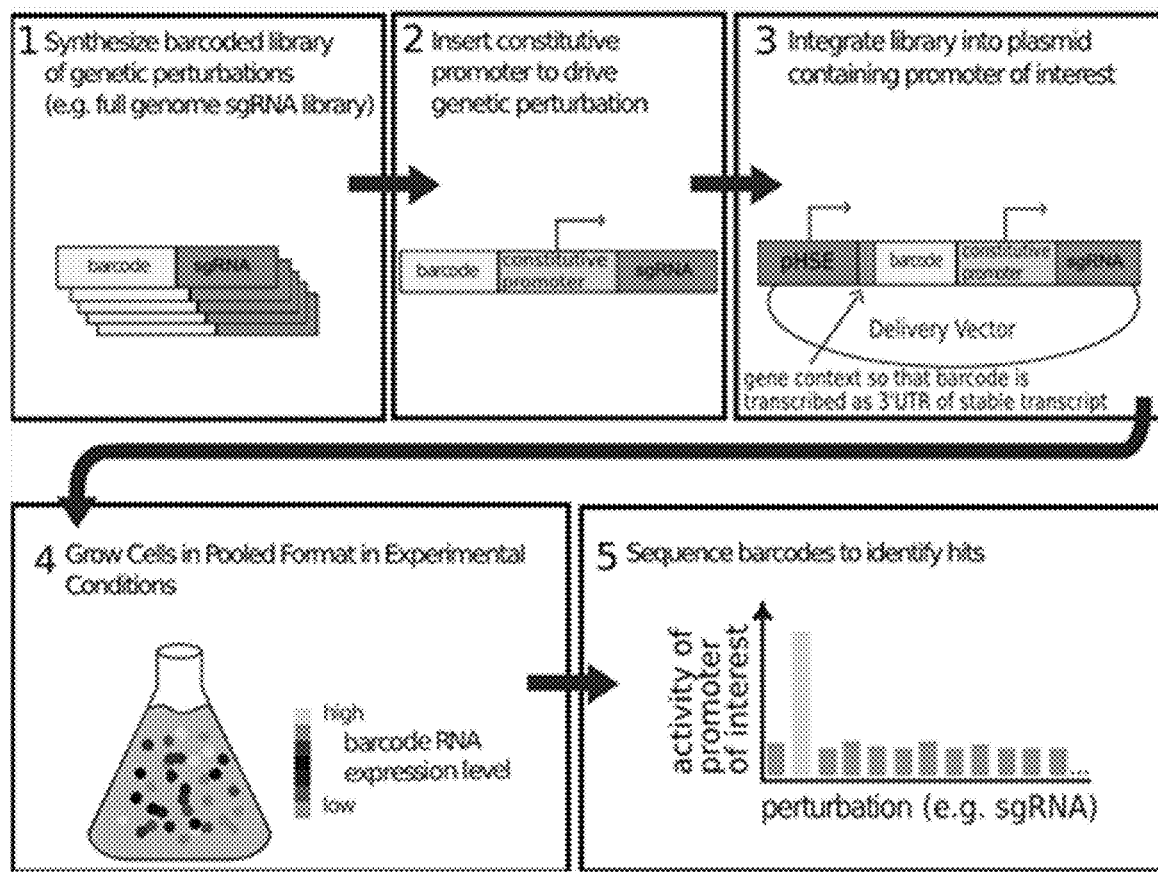
FIG. 2 is a schematic showing the use of an exemplary method provided herein employing barcodes and single guide RNAs (sgRNAs).

A method has been developed and described herein that combines the multiplexing power of pooled high-complexity CRISPRi screens with the resolution of high-content measurement assays. This strategy, referred to as induced barcoding, a schematic of which is shown in FIG. 2, employs five major steps, harnessing deep sequencing to measure the transcription of stress-responsive promoters in the context of specific genome-wide genetic perturbations.

More specifically, a library of DNA constructs is assembled that contains one genetic perturbation (e.g. a single guide RNA (sgRNA) targeting a specific gene) and one DNA barcode (e.g., approximately 20 nucleotides) per construct. To cover an entire genome, this library will consist of between 35,000 (yeast) and 100,000 (human) uniquely barcoded constructs (approximately 5 per gene), each targeting a different sequence in the transcriptome. Each library construct is relatively short (e.g., <200 nucleotides), and therefore the library can be synthesized at reasonable cost by several industrial suppliers. Second, a constitutive promoter is cloned into the library to drive expression of the genetic perturbation using commercial Gateway® cloning (Life Technologies, Carlsbad, Calif.). Third, the constructs are ligated into a delivery vector (CEN/ARS plasmid for yeast, lentiviral for human); a pathway-specific promoter from the delivery vector now drives expression of the barcode. The barcode is placed in the 3' UTR of a stable transcript (e.g. GFP) to ensure expression as a stable mRNA. Fourth, a culture of cells is infected such that approximately one construct is incorporated into each cell. For yeast, this is ensured with a CEN/ARS construct. For lentiviral delivery, this strategy can be approximated by titrating the infection to a multiplicity of infection of greater than 1. Although some subset of the population will be infected by two viruses, this issue is unlikely to become significant because (1) most perturbation constructs in a full-genome set do not affect the pathway readout (HSF1) and (2) co-infection of two specific constructs will not be systematic and will instead create outlier effects that can be averaged out. Fifth, cells are lysed, and RNA and DNA are extracted. Deep sequencing is used to count the frequencies of RNA barcodes (barcodes transcription is proportional to promoter activity) and DNA barcodes (approximately one per cell). The ratio of RNA/DNA for each barcode reveals its enrichment under a specific perturbation and thus pathway activity in that condition. Genetic perturbations will potentially modulate upstream signaling pathways; barcode transcription will be increased by perturbations that increase pathway activity and decreased by perturbations that decrease pathway activity. Note that since enrichment is an average of many cells, the effects of outliers (e.g. cells that harbor two reporter constructs or bursts in transcription) will be mitigated.

Figures 3A, 3B:
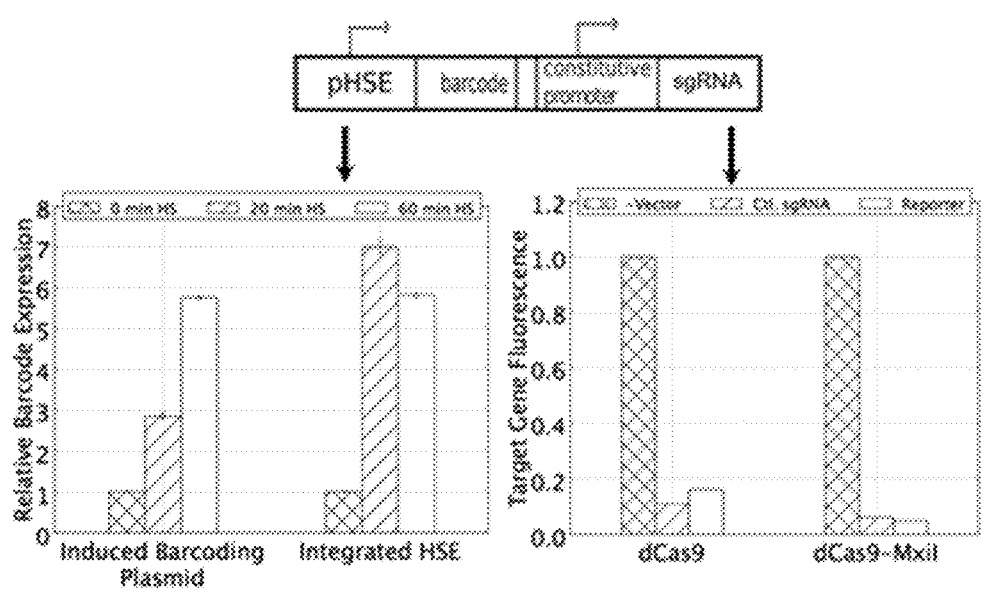
FIGS. 3A and 3B are graphs showing induced-barcoding strategy in yeast to pair a perturbation with a pathway-specific transcriptional readout. A CEN-ARS plasmid encoding a cassette that includes an HSF1 reporter (pHSE) adjacent to a Clustered Regularly Interspaced Short Palindromic Repeats interference (CRISPRi) perturbation was introduced into yeast encoding a Venus fluorescent protein at the endogenous TEF1 locus.

FIG. 3 displays mRNA levels for a barcode induced by mild heat shock in yeast. Barcode levels rise 5-fold in the synthetic, plasmid-based reporter, comparable to a genomically integrated Heat Shock Element (HSE) reporter. The plasmid-based induced-barcode reporter includes a functional genetic perturbation cassette that drives the expression of a sgRNA that can participate in CRISPRi, successfully knocking down the expression of an endogenous gene (FIGS. 3A and 3B). A paired perturbation/readout construct encoded on plasmid was created that can be easily transformed into yeast (FIGS. 3A and 3B). This plasmid includes a CEN/ARS region that ensures about approximately 1 copy of the plasmid per cell. The perturbation element used was a validated single guide RNA (sgRNA) targeting the TEF1 gene. When this perturbation is coexpressed in cells with dead Cas9 (dCas9), the TEF1 gene is repressed (see, Gilbert et al., Cell 154(2):442-51 (2013)). For the readout, a validated Heat shock factor 1 (HSF1) reporter (HSE) was used (see, Brandman et al., Cell 151(5):1042-54 (2012)), which drives green fluorescent protein (GFP) and is induced when cells are subjected to heat shock. In the provided paired/perturbation construct, the HSE reporter was designed to drive GFP as well as a barcode. To test if the sgRNA perturbation worked, the reporter was introduced into a strain of yeast where the coding sequence of the TEF1 gene was replaced by Venus fluorescent protein. This strain has been used in a previous study to test the efficacy of the sgRNA system (Gilbert et al., Cell 154(2):442-51 (2013)). The construct successfully reduced Venus levels as intended (FIGS. 3A and 3B) and the perturbation construct therefore works in the context the paired perturbation/readout construct and its delivery plasmid. It was then determined if an HSE readout worked by measuring RNA barcode levels before and after heatshock for the validated HSE (integrated at the URA3 locus) and our perturbation/readout construct. After 60 minutes heat shock, barcode levels in both the validated HSE and our perturbation/readout construct increased to equivalent levels (FIG. 3A). Therefore, both the perturbation element and readout work in the paired perturbation/readout construct created. Thus, provided herein is a method of creating and using a library of these plasmids that encode sgRNAs targeting all endogenous genes.

EMBODIMENTS

Embodiment 1

A method of multiplexed detection of modulation of transcriptional activity caused by a plurality of perturbation elements, said method comprising:

(i) introducing a plurality of delivery vectors into a cell culture, wherein each delivery vector within said plurality of delivery vectors individually comprises (a) a perturbation element identifying DNA sequence operatively linked to a promoter of interest; and (b) a perturbation element-encoding DNA sequence operatively linked to a constitutive promoter; and wherein said cells of said cell culture integrate one delivery vector per cell;

(ii) allowing said cell culture to express said plurality of delivery vectors, wherein said expression forms a plurality of perturbation element identifying RNA sequences from said perturbation element identifying DNA sequences and a plurality of perturbation elements from said perturbation element-encoding DNA sequences;

(iii) allowing each perturbation element within said plurality of perturbation elements to modulate transcriptional activity of each corresponding promoter of interest;
(iv) detecting an amount of each perturbation element identifying RNA sequence within said plurality of perturbation element identifying RNA sequences;
(v) comparing said amount of each perturbation element identifying RNA sequence within said plurality of perturbation element identifying RNA sequences to an amount of each corresponding perturbation element identifying DNA sequences, thereby detecting modulation of transcriptional activity caused by each of said plurality of perturbation elements.

Embodiment 2

The method of embodiment 1, wherein said perturbation element identifying DNA sequence is about 15 nucleotides to about 500 nucleotides in length.

Embodiment 3

The method of embodiment 2, wherein said perturbation element identifying DNA sequence is about 15 to about 100 nucleotides in length.

Embodiment 4

The method of embodiment 2, wherein said perturbation element identifying DNA sequence is about 20 nucleotides in length.

Embodiment 5

The method of embodiment 4, wherein each delivery vector within said plurality of delivery vectors further comprises an auxiliary-DNA sequence operatively linked to said perturbation element identifying DNA sequence.

Embodiment 6

The method of embodiment 5, wherein said auxiliary-DNA sequence is operatively linked to a 5' end of said perturbation element identifying DNA sequence.

Embodiment 7

The method of embodiment 6, wherein said perturbation element identifying DNA sequence is located in the 3'-UTR of said auxiliary-DNA sequence.

Embodiment 8

The method of embodiment 1, wherein said plurality of delivery vectors are viral plasmids, 2-micron plasmids, or CEN/ARS plasmids.

Embodiment 9

The method of embodiment 8, wherein said plurality of delivery vectors are viral plasmids.

Embodiment 10

The method of embodiment 9, wherein said plurality of delivery vectors are lentiviral delivery vectors.

Embodiment 11

The method of embodiment 1, wherein said promoter of interest is operatively linked to a 5' end of said perturbation element identifying DNA sequence, wherein said constitutive promoter is linked to a 3' end of said perturbation element identifying DNA sequence, and wherein said perturbation element-encoding DNA sequence is operatively linked to a 3' end of said constitutive promoter.

Embodiment 12

The method of embodiment 1, wherein said plurality of perturbation elements comprises shRNA, miRNA, siRNA or CRISPR guide RNA.

Embodiment 13

The method of embodiment 1, wherein said plurality of perturbation elements comprises a protein-perturbation element.

Embodiment 14

The method of embodiment 1, wherein said detecting an amount of each perturbation element identifying RNA sequence within said plurality of perturbation element identifying RNA sequences comprises sequencing said plurality of perturbation element identifying RNA sequences and counting the frequency of each perturbation element identifying RNA sequence within said plurality of perturbation element identifying RNA sequences.

Embodiment 15

The method of embodiment 14, wherein an increased count of a perturbation element identifying RNA sequence relative to an amount of its corresponding perturbation element identifying DNA sequence indicates increased transcriptional activity.

Embodiment 16

The method of embodiment 1, wherein said cell is a terminally differentiated cell.

Embodiment 17

A method of multiplexed quantitative detection of modulation of transcriptional activity caused by a plurality of perturbation elements, said method comprising:
(i) introducing a plurality of delivery vectors into a cell culture, wherein each delivery vector within said plurality of delivery vectors individually comprises (a) a perturbation element identifying DNA sequence operatively linked to a promoter of interest; and (b) a RNA-perturbation element-encoding DNA sequence operatively linked to a constitutive promoter; and wherein said cells of said cell culture integrate one delivery vector per cell;
(ii) allowing said cell culture to express said plurality of delivery vectors, wherein said expression forms a plurality of perturbation element identifying RNA sequences from said perturbation element identifying DNA sequences and a plurality of RNA-perturbation elements from said perturbation element-encoding DNA sequences;
(iii) allowing each RNA-perturbation element within said plurality of perturbation elements to modulate transcriptional activity of each corresponding promoter of interest;
(iv) lysing the cells in the cell culture and extracting nucleic acids;

(v) sequencing each perturbation element identifying RNA sequence within said plurality of perturbation element identifying RNA sequences, thereby determining an amount of each perturbation element identifying RNA sequence;

(v) comparing said amount of each perturbation element identifying RNA sequence to an amount of each corresponding perturbation element identifying DNA sequences, thereby quantitatively detecting modulation of transcriptional activity caused by each of said plurality of perturbation elements.

Embodiment 18

A DNA construct comprising a perturbation element identifying DNA sequence operatively linked to a promoter of interest and a perturbation element-encoding DNA sequence operatively linked to a constitutive promoter, wherein said perturbation element identifying DNA sequence operatively linked to a promoter of interest and said perturbation element-encoding DNA sequence operatively linked to a constitutive promoter are operatively linked.

Embodiment 19

A kit for multiplexed quantitative detection of modulation of transcriptional activity caused by a plurality of perturbation elements, said kit comprising:
(i) a plurality of delivery vectors, wherein each delivery vector within said plurality of delivery vectors individually comprises (a) a perturbation element identifying DNA sequence operatively linked to a promoter of interest; and (b) a perturbation element-encoding DNA sequence operatively linked to a constitutive promoter;
(ii) a first oligonucleotide primer substantially complementary to and hybridizable with said perturbation element identifying DNA sequence; and
(iii) a second oligonucleotide primer substantially complementary to and hybridizable with a perturbation element identifying RNA sequence expressed from said perturbation element identifying DNA sequence.

Embodiment 20

The kit of embodiment 19, further comprising a third oligonucleotide primer substantially complementary to and hybridizable with said perturbation element-encoding DNA sequence.

What is claimed is:

1. A method of multiplexed detection of modulation of transcriptional activity caused by a plurality of perturbation elements, said method comprising:
(i) introducing a plurality of different delivery vectors into a cell culture comprising cells, wherein each delivery vector within said plurality of different delivery vectors individually comprises:
  (a) a perturbation element-encoding DNA sequence encoding a perturbation element, wherein each of said plurality of different delivery vectors comprises a different perturbation element-encoding DNA sequence;
  (b) a perturbation element identifying DNA sequence, wherein the perturbation element identifying DNA sequence identifies the perturbation element-encoding DNA sequence present on the vector;
  (c) a promoter of interest operatively linked to the perturbation element identifying DNA sequence; and
  (d) a constitutive promoter operatively linked to the perturbation element-encoding DNA sequence;
  wherein each perturbation element comprises a shRNA, miRNA, siRNA, CRISPR guide RNA, antisense molecule, or ribozyme; and
  wherein said cells of said cell culture integrate one delivery vector per cell, thereby forming a plurality of vector-containing cells;
(ii) culturing said cell culture such that said plurality of vector-containing cells express a plurality of perturbation element identifying RNA sequences from said perturbation element identifying DNA sequences and a plurality of perturbation elements from said perturbation element-encoding DNA sequences, and further wherein at least a subset of perturbation elements within said plurality of perturbation elements modulate transcriptional activity of the corresponding promoter of interest; and
(iii) detecting an amount of each perturbation element identifying RNA sequence within said plurality of perturbation element identifying RNA sequences;
(iv) detecting an amount of each perturbation element identifying DNA sequence in the plurality of vector-containing cells; and
(v) comparing said amount of each perturbation element identifying RNA sequence within said plurality of perturbation element identifying RNA sequences to an amount of each corresponding perturbation element identifying DNA sequence, thereby detecting modulation of transcriptional activity caused by each of said plurality of perturbation elements,
wherein a higher amount of perturbation element identifying RNA sequence compared to a control is indicative of activation of the promoter of interest by the perturbation element, and a lower amount of perturbation element identifying RNA sequence compared to a control is indicative of repression of the promoter of interest by the perturbation element.

2. The method of claim 1, wherein said perturbation element identifying DNA sequence is about 15 nucleotides to about 500 nucleotides in length.

3. The method of claim 2, wherein said perturbation element identifying DNA sequence is about 15 to about 100 nucleotides in length.

4. The method of claim 2, wherein said perturbation element identifying DNA sequence is about 20 nucleotides in length.

5. The method of claim 4, wherein each delivery vector within said plurality of delivery vectors further comprises an auxiliary-DNA sequence operatively linked to said perturbation element identifying DNA sequence.

6. The method of claim 5, wherein said auxiliary-DNA sequence is operatively linked to a 5' end of said perturbation element identifying DNA sequence.

7. The method of claim 6, wherein said perturbation element identifying DNA sequence is located in the 3'-UTR of said auxiliary-DNA sequence.

8. The method of claim 1, wherein said plurality of delivery vectors are viral plasmids, 2-micron plasmids, or CEN/ARS plasmids.

9. The method of claim 8, wherein said plurality of delivery vectors are viral plasmids.

10. The method of claim 9, wherein said plurality of delivery vectors are lentiviral delivery vectors.

11. The method of claim 1, wherein said promoter of interest is operatively linked to a 5' end of said perturbation element identifying DNA sequence, wherein said constitutive promoter is linked to a 3' end of said perturbation element identifying DNA sequence, and wherein said perturbation element-encoding DNA sequence is operatively linked to a 3' end of said constitutive promoter.

12. The method of claim 1, wherein said plurality of perturbation elements comprises shRNA, miRNA, siRNA or CRISPR guide RNA.

13. The method of claim 1, wherein said detecting an amount of each perturbation element identifying RNA sequence within said plurality of perturbation element identifying RNA sequences comprises sequencing said plurality of perturbation element identifying RNA sequences and counting the frequency of each perturbation element identifying RNA sequence within said plurality of perturbation element identifying RNA sequences.

14. The method of claim 13, wherein an increased count of a perturbation element identifying RNA sequence relative to an amount of its corresponding perturbation element identifying DNA sequence indicates increased transcriptional activity.

15. The method of claim 1, wherein said cell is a terminally differentiated cell.

16. A method of multiplexed quantitative detection of modulation of transcriptional activity caused by a plurality of perturbation elements, said method comprising:
(i) introducing a plurality of different delivery vectors into a cell culture comprising cells, wherein each delivery vector within said plurality of different delivery vectors individually comprises:
　(a) a RNA-perturbation element-encoding DNA sequence encoding a perturbation element, wherein each of said plurality of different delivery vectors comprises a different perturbation element identifying DNA sequence and a different RNA-perturbation element-encoding DNA sequence;
　(b) a perturbation element identifying DNA sequence, wherein the perturbation element identifying DNA sequence identifies the perturbation element-encoding DNA sequence present on the vector;
　(c) a promoter of interest operatively linked to the perturbation element identifying DNA sequence; and
　(d) a constitutive promoter operatively linked to the perturbation element-encoding DNA sequence;
　wherein each perturbation element comprises a shRNA, miRNA, siRNA, CRISPR guide RNA, antisense molecule, or ribozyme; and
wherein said cells of said cell culture integrate one delivery vector per cell, thereby forming a plurality of vector-containing cells;
(ii) culturing said cell culture such that said plurality of vector-containing cells express a plurality of perturbation element identifying RNA sequences from said perturbation element identifying DNA sequences and a plurality of RNA-perturbation elements from said perturbation element-encoding DNA sequences, and further wherein at least a subset of RNA-perturbation elements within said plurality of perturbation elements modulate transcriptional activity of the corresponding promoter of interest;
(iii) lysing the cells in the cell culture and extracting nucleic acids;
(iv) sequencing each perturbation element identifying RNA sequence within said plurality of perturbation element identifying RNA sequences, thereby determining an amount of each perturbation element identifying RNA sequence;
(v) detecting an amount of each perturbation element identifying DNA sequence within said plurality of perturbation element identifying DNA sequences; and
(vi) comparing said amount of each perturbation element identifying RNA sequence to the amount of each corresponding perturbation element identifying DNA sequence, thereby quantitatively detecting modulation of transcriptional activity caused by each of said plurality of perturbation elements,
wherein a higher amount of perturbation element identifying RNA sequence compared to a control is indicative of activation of the promoter of interest by the perturbation element, and a lower amount of perturbation element identifying RNA sequence compared to a control is indicative of repression of the promoter of interest by the perturbation element.

* * * * *